United States Patent [19]

Jikihara et al.

[11] 4,028,091

[45] June 7, 1977

[54] HERBICIDAL COMPOSITION

[75] Inventors: Kazuo Jikihara, Kakegawa; Shinichi Iori, Ogasa; Ichiro Kimura, Shizuoka; Kyoichi Adachi, Yaizu, all of Japan

[73] Assignee: Kumiai Chemical Industry Co., Ltd., Tokyo, Japan

[22] Filed: Sept. 2, 1975

[21] Appl. No.: 609,725

[30] Foreign Application Priority Data

Sept. 2, 1974 Japan .............................. 49-100695

[52] U.S. Cl. ........................................ 71/94; 71/88; 71/93; 71/100; 71/106; 71/118; 71/120; 71/92

[51] Int. Cl.$^2$ .......................................... A01N 9/12

[58] Field of Search .................. 71/94, 100, 88, 92

[56] References Cited

UNITED STATES PATENTS

| 3,682,616 | 8/1972 | Kimura et al. ...................... 71/100 |
| 3,746,532 | 7/1973 | Kimura et al. ...................... 71/100 |

FOREIGN PATENTS OR APPLICATIONS

| 1,088,981 | 10/1967 | United Kingdom ................... 71/94 |

*Primary Examiner*—Glennon H. Hollrah
*Attorney, Agent, or Firm*—Oblon, Fisher, Spivak, McClelland & Maier

[57] ABSTRACT

A herbicidal composition comprises a bipyridylium salt and a thiocarbamate having the formula

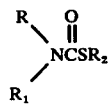

wherein R and $R_1$ each represent a lower alkyl group which in combination with each other can form a heterocyclic ring with the N atom; $R_2$ represents

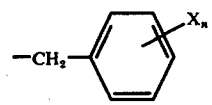

and X represents a halogen atom or a lower alkyl group; and $n$ represents 0, 1 or 2.

9 Claims, No Drawings

HERBICIDAL COMPOSITION

BACKGROUND OF THE INVENTION

1. Field of the Invention

The present invention relates to a new herbicidal composition which is effective for both foliage treatment and soil treatment in agricultural areas such as orchards, upland fields, paddy fields and the like, and also in non-agricultural areas.

2. Description of the Prior Art

In general, it takes relatively less time to cultivate an orchard as compared with the time required for cultivation in other agricultural areas. However, in many cases, the orchard is developed adjacent to a forest and/or a wasteland. In these situations, many weeds are extended from the forest and/or wasteland into the orchard. Accordingly, various weeds, such as annual weeds, e.g., Manna-grass, Barnyard grass, Smartweed, and the like; perennial weeds, i.e., Field horsetail, Culy dock, *Cayratia japonica*, Bindweed, and the like, and coppice appear. Some of these weeds grow very high and/or in high multiplication. Some weeds appear in the areas immediately surrounding the trees. The following problems, associated with the yield of the fruit and the control and tending of the operation, are caused by the presence of these weeds:

1. The control and tending operations are disturbed.
2. The effects of the wind and sunlight are diminished.
3. Disease and insect damage are caused and promoted.
4. The nutritional value of fertilizer is lost.
5. Water in the soil is used up, causing drought injury.

In the conventional methods of inhibition of the weeds, it has been known to apply foilage-treatment type herbicides such as 1,1'-dimethyl-4,4'-bypyridylium dichloride or a mixture of 3,4-dichloropropionanilide and α-naphthyl N-methylcarbamate in the growing period of the weeds, or to apply soil-treatment type herbicides such as 3-(3,4-dichlorophenyl)-1,1-dimethylurea or 2,4-bis(iso-propylamino)-6-methylthio-1,3,5-triazine, and the like before the weed seedlings appear. When the soil-treatment type herbicides are applied, the active ingredient is translocated in the soil and is absorbed by the roots of the trees, causing phytotoxicity. Also, the herbicidal effect is disadvantageously varied by changing said conditions, such as the water content of the soil. On the other hand, when the foilage-treatment type herbicides are applied, the herbicidal effect is relatively stable and confirmation of its efficacy can easily be made. Retreatments can then be made accordingly. As a result, foilage-treatment type herbicides such as 1,1'-dimethyl-4,4'-bipyridylium dichloride and a mixture of 3,4-dichloropropionanilide and α-naphthyl N-methylcarbamate have been used primarily. However, when 1,1'-dimethyl-4,4'-bipyridylium dichloride is used, the herbicidal effect against grown weeds in inferior. It is considered that this defect is caused by small translocation of the active ingredient into the bodies of the plants. Only the cells of the weeds in the immediate vicinity of the point of contact of the active ingredient are damaged under conditions of intense irradiation. The translocation of the active ingredient in the weeds is quite slow, causing an inferior effect. The herbicidal effect is also disadvantageously decreased by rain-fall after the application. In such cases, the regrowth of the weeds is rapid, whereby the purpose of the application of the herbicide cannot be attained. Accordingly, sequential applications of the herbicides are necessitated. Consequently, a need continues to exist for an effective herbicide especialy for use in an orchard against grown weeds.

SUMMARY OF THE INVENTION

Accordingly, it is an object of the present invention to provide a herbical composition which is effective for inhibiting the growth of weeds in the growth stage as well as weeds in other stages in both agricultural and non-agricultural areas, especially in orchards.

Briefly, this and other objects of this invention, as will hereinafter become clear from the ensuing discussion, have been attained by providing a herbicidal composition which comprises a bipyridylium salt of 1,1'-dimethyl-4,4'-bipyridylium or 1,1'-ethylene-2,2'-bipyridylium and a thiocarbamate having the formula

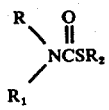

wherein R and $R_1$ each represent a lower alkyl group having 1 – 7 carbon atoms which in combination with each other can form a heterocyclic ring with the N atom; $R_2$ represents

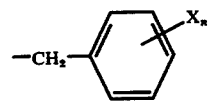

wherein X represents a halogen atom such as F, Cl, Br, or I, or a lower alkyl group, having 1 – 7 carbon atoms and $n$ represents 0, 1 or 2.

DETAILED DESCRIPTION OF THE PREFERRED EMBODIMENTS

The thiocarbamates used in this invention have a relatively low herbicidal effect in foliage treatment when used alone. Accordingly, heretofore, it has been considered nearly impossible to improve the herbicidal effect in foliage treatment by combination with other herbicides. The present invention has been attained by the discovery of a special synergistic effect resulting from the combination of the specific bypyridylium salts and the specific thiocarbamates mentioned above. The surprising synergistic effects imparted by the combination of these ingredients are as follows:

1. The herbicidal drought effect of the specific bipyridylium salt when used alone is remarkably improved. Effective results can be attained by using an amount of the specific bipyridylium salt which is only ½ – ¼ of the amount required when the salt is used alone.
2. The herbicidal effect against weeds in the grown stage is remarkably improved. The weed-growth inhibiting period is prolonged by prevention of the regrowth of the weeds.
3. The herbicidal effect is improved, even when it is applied under intense irradiation.
4. The decrease in the herbicidal effect caused by rainfall after application is negligible.

It is considered that the above-mentioned effects are effected by promoting the absorption and translocation of the specific bipyridylium salt into the body of plants by synergistic action with the specific thiocarbamate, and also by promoting the herbicidal effect of the specific bipyridylium salt in the body of the plant. The specific thiocarbamate itself imparts a herbicidal effect in soil-treatment in addition to the above-mentioned synertistic effects to control the growth of weeds in the soil. Accordingly, the herbicidal composition of this invention is an ideal herbicidal composition for both foliage and soil-treatment. Among other things, the synergistic effects could not be expected because of the specific thiocarbamate is a soil-treating agent and the herbicidal effect is produced by inhibition of protein production in plants.

In the herbicidal composition of this invention, the ratio of the bipyridylium salt to the thiocarbamate should be 1 : 1 ~ 100, preferably 5 ~ 30. In foliage treatment, the amount of the bipyridylium salt should be 5 – 500 g/10 ares, preferably 10 –50 g/10 ares, and the amount of the thiocarbamate should be 20 – 500 g/10 ares, preferably 100–300 g/10 ares. In soil treatment, the amount of the pyridylium salt should be 5 – 500 g/10 ares, preferably 10 – 50 g/10 ares, and the amount of the thiocarbamate should be 50 – 1000 g/10 ares, preferably 200–600 g/10 ares.

Suitable bipyridylium salt include the dichloride and dibromide of 1,1'-dimethyl-4,4'-bipyridylium or 1,1'-ethylene-2,2'-bipyridylium; that is,

COMPOUND A 1,1'-dimethyl-4,4'-dipyridylium dichloride

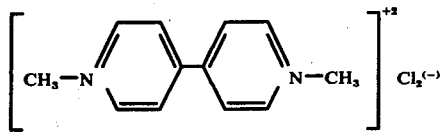

COMPOUND B 1,1'-dimethyl-4,4'-bipyridylium dibromide

COMPOUND C 1,1'-ethylene-2,2'-bipyridylium dichloride

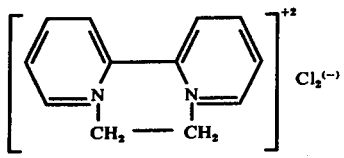

COMPOUND D 1,1'-ethylene-2,2'-bipyridylium dibromide.

Suitable thiocarbamates include the following:

COMPOUND 1

S-benzyl-N,N-di-n-propylthiolcarbamate; b.p. 123°–125° C/0.015 mm Hg.

COMPOUND 2

S-(4-methylbenzyl)-N,N-diethylthiolcarbamate; b.p. 107°–115° C/0.002 mm Hg.

COMPOUND 3

S-(4-chlorobenzyl)-N-hexamethyleneiminocarbothiolate; m.p. 53°–55° C.

COMPOUND 4

S-(2-chlorobenzyl)-N,N-diethylthiocarbamate; b.p. 136°–140° C/0.04-0.05 mm Hg.

COMPOUND 5

S-(2.5-dimethylbenzyl)-N,N-dimethylthiolcarbamate; b.p. 130°–140° C/0.012 mm Hg.

COMPOUND 6

S-(4-chlorobenzyl)-N,N-diethylthiocarbamate; b.p. 127°–131° C/0.012 mm Hg.

The herbicidal compositions of this invention impart excellent herbicidal effects when applied to gramineous weeds, broadleaf weeds, perennial weeds and the like on agricultural areas such as upland fields, paddy fields, as well as orchards, and on non-agricultural areas. In applying the two active ingredients, it is also possible to prepare two compositions each containing one of the active ingredients of the bipyridylium salt and the thiocarbamate. The two compositions can then be combined in the application so as to produce a mixture in the above-mentioned ratio. The active ingredients can be applied using conventional techniques such as by adding a solid or liquid diluent or a surfactant and diluting with water.

Having now generally described the invention, a further understanding can be obtained by reference to certain specific Examples and Experiments, which are provided herein for purposes of illustration only and are not intended to be limiting in any manner unless otherwise specified.

PREARATION OF COMPOSITION 1

Wettable Powder 40 wt. parts of Compound 1, 10 wt. parts of Compound B, 2 wt. parts of polyoxyethylenealkyarylether, 2 wt. parts of polyvinyl alcohol, 25 wt. parts of silicon dioxide and 21 wt. parts of diatomaceous earth were uniformly mixed and crushed to yield a wettable powder.

PREPARATION OF COMPOSITION 2

Emulsion 40 wt. parts of Compound 2, 10 wt. parts of Compound A, 10 wt. parts of polyoxyethylenealkyl phenol and 40 wt. parts of methanol were mixed and diluted with water to yield an emulsion.

PREPARATION OF COMPOSITION 3

Wettable Powder 25 wt. parts of Compound 3, 25 wt. parts of Compound C, 2 wt. parts of polyoxyethylenealkylarylether, 2 wt. parts of polyvinyl alcohol and 46 wt. parts of diatomaceous earth were uniformly mixed and crushed to yield a wettable powder.

PREPARATION OF COMPOSITION 4

Wettable Powder 30 wt. parts of Compound 4, 15 wt. parts of Compound D, 2 wt. parts of sodium alkylacrylsulfonate, 2 wt. parts of polyvinyl alcohol, 10 wt. parts of silicon dioxide and 41 wt. parts of diatomaceous earth were uniformly mixed and crushed to yield a wettable powder.

PREPARATION OF COMPOSITION 5

Emulsion 40 wt. parts of Compound 5, 5 wt. parts of Compound A, 7 wt. parts of polyoxyethylenealkylarylether, 3 wt. parts of calcium alkylbenzene sulfonate and 45 wt. parts of methanol were mixed and diluted with water to yield an emulsion.

The effect of the herbicidal compositions of this invention will be illustrated by certain experiments, which are not intended to be limiting unless otherwise specified.

EXPERIMENT 1

Manna-grass (height of 25 – 30 cm) and Pig weed (height of 25 – 30 cm) grown in pots of 100 cm$^2$ area were used for the experiments. The herbicidal compositions containing the amounts of the active ingredients specified in Table 1 were diluted with water. The diluted compositions were uniformly sprayed by a microsprayer at a rate of 100 liter/10 ares. The tests were performed twice in a greenhouse. After 15 days following the application, the weed above the earth were cut, dried and weighed. The percentage of the weight of the dried weeds in the treated fields to that of the non-treated fields was calculated. Compositions prepared by mixing Compound A (an emulsion containing 24% of the active ingredient) or Compound D (an emulsion containing 30% of the active ingredient) and each of several thiocarbamates (an emulsion containing 50% of the active ingredient) in a tank were used. The applications of the compositions were conducted from 3:00 to 4:00 p.m. under an irradiation intensity of 30,000 Lux. The treating compositions and results are shown in Table 1.

Table 1

| Active ingredient | Amount of emulsions | | | Manna-grass (%) | Pig-weed (%) |
|---|---|---|---|---|---|
| Compound A | Ⓐ 200cc | + | ① 400cc | 0 | 0 |
| | 100 | + | 200 | 5 | 8 |
| + | 50 | + | 100 | 18 | 21 |
| Compound 1 | 25 | + | 100 | 33 | 46 |
| Compound A | Ⓐ 200cc | + | ② 400cc | 0 | 0 |
| | 100 | + | 200 | 0 | 3 |
| + | 50 | + | 100 | 3 | 16 |
| Compound 2 | 25 | + | 100 | 31 | 38 |
| Compound A | Ⓐ 200cc | + | ③ 400cc | 0 | 0 |
| | 100 | + | 200 | 0 | 8 |
| + | 50 | + | 100 | 6 | 21 |
| Compound 3 | 25 | + | 50 | 42 | 47 |
| Compound A | Ⓐ 200cc | + | ④ 400cc | 0 | 0 |
| | 100 | + | 200 | 0 | 4 |
| + | 50 | + | 100 | 11 | 17 |
| Compound 4 | 25 | + | 50 | 36 | 51 |
| Compound A | Ⓐ 200cc | + | ⑤ 400cc | 0 | 0 |
| | 100 | + | 200 | 0 | 0 |
| + | 50 | + | 100 | 3 | 11 |
| Compound 5 | 25 | + | 50 | 18 | 30 |
| Compound A | Ⓐ 200cc | + | ⑥ 400cc | 0 | 0 |
| | 100 | + | 200 | 0 | 0 |
| + | 50 | + | 100 | 5 | 8 |
| Compound 6 | 25 | + | 50 | 12 | 16 |
| Compound D | Ⓓ 200cc | + | ① 400cc | 0 | 0 |
| | 100 | + | 200 | 0 | 0 |
| + | 50 | + | 100 | 3 | 14 |
| Compound 1 | 25 | + | 50 | 24 | 29 |
| Compound D | Ⓓ 200cc | + | ③ 400cc | 0 | 0 |
| | 100 | + | 200 | 0 | 1 |
| + | 50 | + | 100 | 5 | 15 |
| Compound 3 | 25 | + | 50 | 29 | 26 |

Table 1-continued

| Active ingredient | Amount of emulsions | | | Manna-grass (%) | Pig-weed (%) |
|---|---|---|---|---|---|
| Compound D | Ⓓ 200cc | + | ⑥ 400cc | 0 | 0 |
| | 100 | + | 200 | 0 | 0 |
| + | 50 | + | 100 | 2 | 0 |
| Compound 6 | 25 | + | 50 | 10 | 6 |
| Compound 1 | 800 | | | 92 | 100 |
| | 400 | | | 100 | 100 |
| | 200 | | | 100 | 100 |
| | 100 | | | 100 | 100 |
| Compound 2 | 800 | | | 88 | 96 |
| | 400 | | | 97 | 100 |
| | 200 | | | 100 | 100 |
| | 100 | | | 100 | 100 |
| Compound 3 | 800 | | | 93 | 97 |
| | 400 | | | 98 | 100 |
| | 200 | | | 100 | 100 |
| | 100 | | | 100 | 100 |
| Compound 4 | 800 | | | 98 | 100 |
| | 400 | | | 100 | 100 |
| | 200 | | | 100 | 100 |
| | 100 | | | 100 | 100 |
| Compound 5 | 800 | | | 89 | 90 |
| | 400 | | | 97 | 96 |
| | 200 | | | 100 | 100 |
| | 100 | | | 100 | 100 |
| Compound 6 | 800 | | | 90 | 95 |
| | 400 | | | 100 | 100 |
| | 200 | | | 100 | 100 |
| | 200cc | | | 23 | 52 |
| | 100 | | | 40 | 67 |
| Compound A | 50 | | | 81 | 93 |
| | 25 | | | 100 | 100 |
| | 200 | | | 46 | 41 |
| | 100 | | | 63 | 56 |
| Compound D | 50 | | | 98 | 91 |
| | 25 | | | 100 | 100 |
| Non-treatment | — | | | 100 | 100 |

EXPERIMENT 2

Synergistic Effect (10 days following the application)

An orange orchard wherein various test weeds were uniformly grown was divided into blocks of dimensions 2 m × 4 m. The herbicidal compositions containing amounts of the active ingredients as specified in Table 2 were diluted with water. The diluted compositions were sprayed at a rate of 100 liter/10 ares. After 10 days following the application, the herbicidal effects were observed. The weeds were Manna-grass (height of 40–50 cm); Smartweed (height of 50–70 cm); Hedge bindweed (height of 80–100 cm); and Cagratia japonice (height of 80–120 cm). The herbicidal effects are indicated using the following scale:

0: Number and height of the weeds is the same as that of non-treated block.
1: 80% of the number or height of the weeds as compared with the non-treated block.
2: 60% of the number or height of the weeds as compared with the non-treated block.
3: 40% of the number or height of the weeds as compared with the non-treated block.
4: 20% of the number or height of the weeds as compared with the non-treated block.
5: weeds were completely dead.

The results are shown in Table 2.

Table 2

| Concentration of active ingredients (ppm) | Manna-grass | Smart-weed | Hedge bindweed | Cagratia japonice |
|---|---|---|---|---|
| Compound A | | | | |
| 720 | 3.0 | 2.5 | 3.0 | 3.0 |
| 360 | 1.5 | 1.0 | 1.5 | 2.0 |
| 180 | 0 | 0 | 0.5 | 0.5 |

Table 2-continued

| Concentration of active ingredients (ppm) | Manna-grass | Smart-weed | Hedge bindweed | Cagratia japonice |
|---|---|---|---|---|
| 90 | 0 | 0 | 0 | 0 |
| Compound A + Compound 6 Ⓐ ⑥ | | | | |
| 400 + 1600 | 5 | 5 | 5 | 5 |
| 200 + 800 | 5 | 5 | 5 | 5 |
| 100 + 400 | 5 | 5 | 5 | 5 |
| 50 + 200 | 4.5 | 5 | 5 | 5 |
| Compound 6 | | | | |
| 4000 | 0.5 | 0.5 | 0 | 0 |
| 2000 | 0 | 0 | 0 | 0 |
| 1000 | 0 | 0 | 0 | 0 |
| 500 | 0 | 0 | 0 | 0 |
| Non-treated block | 0 | 0 | 0 | 0 |

EXPERIMENT 3

Regrowth Inhibition of Manna-grass

Manna-grass (height of 30 – 35 cm) grown in pots of 100 $cm^2$ was used for the experiment. The herbicidal compositions containing the amounts of the active ingredients shown in Table 3 were diluted with water. The diluted compositions were uniformly sprayed by a microsprayer at a rate of 100 liter/10 ares during the evening and the treated pots were kept in a greenhouse. Watering was conducted by sucking water from the bottom of each pot. The herbicidal effects were observed and are indicated as in Experiment 2.
The results are shown in Table 3.

Table 3

| Concentration of active ingredients (ppm) | 1 day after application | 5 days after application | 10 days after application | 20 days after application |
|---|---|---|---|---|
| Compound A  360 | 3.5 | 3.5 | 1 | 0 |
| 180 | 2 | 2 | 0 | 0 |
| 90 | 1.5 | 1.5 | 0 | 0 |
| 45 | 0.5 | 0 | 0 | 0 |
| Compound A + Compound 6  Ⓐ ⑥ | | | | |
| 400 + 800 | 5 | 5 | 5 | 5 |
| 200 + 400 | 5 | 5 | 5 | 5 |
| 100 + 200 | 5 | 5 | 5 | 4.5 |
| 50 + 100 | 5 | 5 | 4.5 | 3.0 |
| Compound 6  4000 | 0.5 | 0.5 | 0 | 0 |
| 2000 | 0 | 0 | 0 | 0 |
| 1000 | 0 | 0 | 0 | 0 |

EXPERIMENT 4

Effect of Rain

The test of Experiment 2 was repeated except for the application of artificial rain at a rate of 200 mm/hr. after 15 minutes following the application of the herbicidal compositions. The next day, the herbicidal effects were observed.
The results are shown in Table 4.

Table 4

| Concentration of active ingredients (ppm) | Manna-grass non-rain block | Manna-grass artificial rain block |
|---|---|---|
| Compound A  720 | 4.5 | 3 |
| 360 | 4 | 2 |
| 180 | 3.5 | 1 |
| Compound A + Compound 6  Ⓐ ⑥ | | |
| 600 + 2400 | 5 | 5 |
| 300 + 1200 | 5 | 5 |
| 150 + 600 | 5 | 5 |
| 75 + 300 | 5 | 4.5 |
| Compound 6  4000 | 1.0 | 1.0 |

Table 4-continued

| Concentration of active ingredients (ppm) | Manna-grass non-rain block | Manna-grass artificial rain block |
|---|---|---|
| 2000 | 0 | 0 |
| 1000 | 0 | 0 |

EXPERIMENT 5

Comparison of the Effects of Application at Daytime Versus those at Evening

Manna-grass (height of 30–40 cm) grown in pots of 100 $cm^2$ was used for the experiment. The herbicidal compositions containing the amounts of the active ingredients specified in Table 5 were diluted with water. The diluted compositions were sprayed uniformly by a microsprayer at a rate of 10 liter/10 ares. The applications were conducted under an irradiation intensity of 50,000 lux of sunlight at daytime and a 2,500 lux at evening. After 5 days following the application, the herbicidal effects were observed and are indicated as in Experiment 2.
The results are shown in Table 5.

Table 5

| Concentration of active ingredients (ppm) | 50,000 lux irradiation Manna-grass | 2,500 lux irradiation Manna-grass |
|---|---|---|
| Compound A  720 | 4 | 4.5 |
| 620 | 3 | 4 |
| 180 | 1.5 | 3.5 |
| Compound A + Compound 6  Ⓐ ⑥ | | |
| 400 + 1600 | 5 | 5 |
| 200 + 800 | 5 | 5 |
| 100 + 400 | 5 | 5 |
| 50 + 200 | 5 | 5 |

Having now fully described the invention, it will be apparent to one of ordinary skill in the art that many changes and modifications can be made thereto without departing from the spirit or scope of the invention as set forth herein.

What is claimed as new and intended to be covered by Letters Patent is:

1. A herbicidal composition, which consists essentially of:
an effective amount of the mixture of a bipyridylium salt selected from the group consisting of the dichloride and dibromide salts of 1,1'-dimethyl-4,4'-bipyridylium and 1,1'-ethylene-2,2'-bipyridylium and a thiocarbamate having the formula $$\begin{array}{c} R \\ \phantom{R} \diagdown \\ \phantom{RRR} NCSR_2 \\ \phantom{R} \diagup \phantom{|} \\ R_1 \phantom{NCSR} \end{array} \begin{array}{c} O \\ \| \\ \phantom{} \end{array}$$

wherein R and $R_1$ each represent a lower alkyl group or which in combination with each other and with the N atom can form a hexamethyleneimino ring, $R_2$ represents $$CH_2 - \bigotimes X_n$$

and X represents a halogen atom of a lower alkyl group, and n represents 0, 1 or 2, wherein the ratio of said bipyridylium salt to said thiocarbamate is 1:1–4.

2. The herbicidal composition of claim 1, which comprises the dichloride or dibromide salt of 1,1'-dimethyl-4,4'-bipyridylium and S-(4-chlorobenzyl)-N,N-diethyl-thiocarbamate as active ingredients.

3. The herbicidal composition of claim 1, wherein X is a chlorine atom or a methyl group.

4. The herbicidal composition of claim 1, wherein all alkyl groups contain from 1 – 7 carbon atoms.

5. The herbicidal composition of claim 2, wherein the active ingredients are in the form of an emulsion.

6. A method of controlling weeds which comprises applying to the locus thereof an effective amount of a diluted solution of the herbicidal composition of claim 1.

7. The method of claim 6, wherein the herbicidal composition is applied to the foliage of the weeds.

8. The method of claim 6, wherein the herbicidal composition is applied to the soil.

9. The method of claim 8, wherein the amount of the bipyridylium salt is 5 – 500 g/10 ares and the amount of the thiocarbamate is 50 – 1000 g/10 ares.

* * * * *